United States Patent
Hoffman et al.

(10) Patent No.: US 8,924,231 B2
(45) Date of Patent: Dec. 30, 2014

(54) HEALTHCARE PROVIDER, ADMINISTRATOR AND METHOD FOR EFFECTUATING A MEDICATION THERAPY MANAGEMENT, ADHERENCE AND PHARMACOSURVEILLANCE PROGRAM

(75) Inventors: Steve Hoffman, Scottsdale, AZ (US); Steve Mink, Scottsdale, AZ (US); Philip Villavicencio, Sparta, NJ (US)

(73) Assignee: McKesson Specialty Arizona Inc., Scottsdale, AZ (US)

( * ) Notice: Subject to any disclaimer, the term of this patent is extended or adjusted under 35 U.S.C. 154(b) by 0 days.

(21) Appl. No.: 13/096,110

(22) Filed: Apr. 28, 2011

(65) Prior Publication Data
US 2011/0202375 A1  Aug. 18, 2011

Related U.S. Application Data

(63) Continuation of application No. 11/693,170, filed on Mar. 29, 2007, now Pat. No. 7,957,983.

(60) Provisional application No. 60/788,266, filed on Mar. 31, 2006.

(51) Int. Cl.
| | |
|---|---|
| *G06Q 40/00* | (2012.01) |
| *G06Q 50/22* | (2012.01) |
| *G06Q 10/08* | (2012.01) |
| *G06Q 50/24* | (2012.01) |
| *G06Q 40/08* | (2012.01) |
| *G06F 19/00* | (2011.01) |

(52) U.S. Cl.
CPC .............. *G06Q 50/22* (2013.01); *G06F 19/322* (2013.01); *G06F 19/3456* (2013.01); *G06F 19/328* (2013.01); *G06Q 10/087* (2013.01); *G06Q 50/24* (2013.01); *G06Q 40/08* (2013.01)
USPC ...................................... 705/2; 705/3; 705/4

(58) Field of Classification Search
CPC . G06F 19/328; G06F 19/322; G06F 19/3456; G06Q 40/08; G06Q 10/087; G06Q 50/22; G06Q 50/24
USPC ......................................................... 705/2–4
See application file for complete search history.

(56) References Cited

U.S. PATENT DOCUMENTS

| | | | |
|---|---|---|---|
| 5,628,530 | A | 5/1997 | Thornton |
| 5,832,449 | A | 11/1998 | Cunningham |

(Continued)

FOREIGN PATENT DOCUMENTS

| | | |
|---|---|---|
| CA | 2 482 370 A1 | 3/2006 |
| WO | WO 95/03569 | 2/1995 |

(Continued)

OTHER PUBLICATIONS

"Telecommunication Standard Implementation Guide Version 5.1", *National Council for Prescription Drug Programs*, Sep. 1999.

(Continued)

*Primary Examiner* — Daniel Felten
(74) *Attorney, Agent, or Firm* — Alston & Bird LLP

(57) ABSTRACT

A method is provided that includes initiating adjudication of a primary claim in response to a purchase transaction at a primary payer for a client at a point of sale of a healthcare provider, and adjudicating one or more services of a program of the administrator to which the client is enrolled and/or one or more secondary benefits following the adjudication of the primary claim. The purchase transaction is applicable to the respective program and the respective secondary benefit, and the program includes one or more services. The method also includes providing the one or more services and/or secondary benefits to the client in response to adjudicating the one or more services and/or secondary benefits.

22 Claims, 4 Drawing Sheets

(56) References Cited

U.S. PATENT DOCUMENTS

| | | | |
|---|---|---|---|
| 6,012,035 | A | 1/2000 | Freeman |
| 6,101,483 | A | 8/2000 | Petrovich |
| 6,112,182 | A | 8/2000 | Akers et al. |
| 6,256,614 | B1 | 7/2001 | Wecker |
| 6,343,271 | B1 * | 1/2002 | Peterson et al. ............. 705/4 |
| 6,757,898 | B1 | 6/2004 | Ilsen et al. |
| 6,769,228 | B1 | 8/2004 | Mahar |
| 7,055,273 | B2 | 6/2006 | Roshkoff |
| 7,155,397 | B2 | 12/2006 | Alexander et al. |
| 7,640,177 | B2 | 12/2009 | Fralic |
| 7,720,697 | B1 | 5/2010 | Silverstein |
| 7,957,983 | B2 | 6/2011 | Hoffman et al. |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0039599 | A1 | 2/2004 | Fralic |
| 2004/0073457 | A1 | 4/2004 | Kalies |
| 2004/0078234 | A1 | 4/2004 | Tallal, Jr. |
| 2004/0111291 | A1 | 6/2004 | Dust et al. |
| 2004/0117323 | A1 | 6/2004 | Mindala |
| 2004/0148198 | A1 | 7/2004 | Kalies |
| 2004/0249745 | A1 | 12/2004 | Baaren |
| 2005/0015280 | A1 | 1/2005 | Gabel et al. |
| 2005/0060201 | A1 | 3/2005 | Connely, III et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0228692 | A1 | 10/2005 | Hodgdon |
| 2005/0240473 | A1 | 10/2005 | Ayers, Jr. et al. |
| 2005/0273387 | A1 | 12/2005 | Previdi |
| 2005/0288972 | A1 | 12/2005 | Marvin et al. |
| 2006/0020514 | A1 | 1/2006 | Yered |
| 2006/0026041 | A1 | 2/2006 | Ullman |
| 2006/0085231 | A1 | 4/2006 | Brofman |
| 2006/0149784 | A1 | 7/2006 | Tholl et al. |
| 2006/0184391 | A1 | 8/2006 | Barre et al. |
| 2006/0259363 | A1 | 11/2006 | Jhetam |
| 2006/0271405 | A1 | 11/2006 | Cipolle et al. |
| 2007/0005402 | A1 | 1/2007 | Kennedy et al. |
| 2007/0050209 | A1 | 3/2007 | Yered |
| 2007/0136100 | A1 | 6/2007 | Daugherty et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |
| 2010/0241445 | A1 | 9/2010 | Rago et al. |

FOREIGN PATENT DOCUMENTS

| | | |
|---|---|---|
| WO | WO 00/39737 | 7/2000 |
| WO | WO 2007/025295 A2 | 3/2007 |

OTHER PUBLICATIONS

"OPUS COREspondent", Newsletter, May/Jun. 2004, can be located at www.opuscore.com/main/newsletters/mayjune2004newsletter.pdf.

Office Action for U.S. Appl. No. 12/409,156 dated Jan. 24, 2011.

Office Action for U.S. Appl. No. 11/693,170 dated Jun. 22, 2010.

Lamb, J.; "E-prescriptions: New era of Eelectronic medicine management"; Financial Times; Published: Feb. 19, 2001; 2 pages.

Sampson, R.J.; "Taking Control of Health Care Costs"; Best's Review—Life Health Insurance Edition; vol. 84; Issue 7; Nov. 1983; pp. 64-66.

ACS to Demonstrate Electronic Health Record Solution Suite at MMIS 2007 Conference; PR Newswire; Aug. 13, 2007; 2 pages.

Medic: On-line Goes In-house; Chain Store Age Executive; vol. 63; Issue 1; USA; Jan. 1987; pp. 128-132.

Pharmacy Industry Leaders Launch Firm to Supply Real-Time Data; PR Newswire; Jul. 30, 2001; 4 pages.

TechRx Announces Successful Beta Deployment of Updated T-Rex (R) One Solution for Independent Pharmacies; Network-Based Pharmacy Application Provides and Easy-to-Learn, Powerful Solution for Independent Pharmacy Users; PR Newswire; May 13, 2002; 2 pages.

Notice of Allowance for U.S. Appl. No. 11/693,170, mailed Jan. 28, 2011.

Office Action for U.S. Appl. No. 12/200,441, mailed Aug. 5, 2009.

Notice of Allowance for U.S. Appl. No. 12/200,441, mailed Jan. 26, 2010.

Office Action for U.S. Appl. No. 12/409,156, dated Aug. 15, 2011.

* cited by examiner

HEALTHCARE PROVIDER, ADMINISTRATOR AND METHOD FOR EFFECTUATING A MEDICATION THERAPY MANAGEMENT, ADHERENCE AND PHARMACOSURVEILLANCE PROGRAM

CROSS REFERENCE TO RELATED APPLICATION(S)

This application is a continuation of U.S. patent application Ser. No. 11/693,170, filed Mar. 29, 2007 now U.S. Pat. No. 7,957,983, which claims the benefit of U.S. Provisional Patent Application No. 60/788,266, filed Mar. 31, 2006, both of which are hereby incorporated herein in their entirety by reference.

FIELD OF THE INVENTION

The present invention generally relates to systems and methods for effectuating a healthcare-related program at least partially based on point-of-service (POS) transactions and, more particularly, to systems and methods for effectuating a medication therapy management, adherence and pharmacosurveillance program at least partially based on a POS transaction at a healthcare provider.

BACKGROUND OF THE INVENTION

For a number of years, pharmaceutical manufacturers have provided patients with personalized marketing services and programs designed to encourage product adoption or promote continued use of their brand medications. These services and programs have included, for example, rebates, point-of-sale free product samples, ATM gift cards, educational mailings and refill reminders. The impact of these programs is diminished, however, when accurate and timely information on the patient's use of the medication before and after the service is unavailable.

Marketing service providers have been unable to directly link any of the above services with a patient's prescription fill history unless they are also a pharmacy, PBM (Pharmacy Benefits Manager) or health plan. These organizations have visibility to their own customer or membership's prescription claim transaction data and can perform educational or other interventional activities in response to prescription fulfillment behavior. They can also measure the impact of those particular activities on subsequent patient prescription utilization. Unfortunately, their reach over a cross-section of a brand pharmaceutical market is limited.

Independent marketing service providers not associated with a particular third-party payer or pharmacy, have alternatively collected prescription utilization information directly from patients in order to trigger marketing services. The methodologies used to capture prescription transaction information, however, may be inadequate to capture timely, accurate and relevant information. Independent marketing service providers do have the ability to access historical prescription data via third party resellers and match it with the specific population of patients participating in a marketing program to measure the impact of their marketing activities. While this data can be meaningful and significant, manufacturers may perceive it to be incomplete or inferior because not all pharmacy transactions are sold to these third parties.

Also for a number of years, pharmaceutical companies have expanded upon the practice of donating free samples of brand medications to physicians for distribution to patients by directly providing patients with mail-in rebates and electronic rebates at the point of sale (provided via certain sample vouchers). More recently, companies have followed trends from other consumer markets by providing monetary incentives in the form of debit "gift" cards or credit card mechanisms.

The incentives provided by these cards have not been linked to the fulfillment of the associated prescription, and in many cases consumers have used the cards to purchase non-pharmaceutical items at their drug retailer or elsewhere. In addition, fraudulent use of the cards has been cited including examples of using the entire balance on a debit card for one (rather than the intended multiple) prescription transaction. This type of abuse is currently being addressed through "instant rebate" debit card programs that allow for only one rebate per store transaction, but the systems and data are still de-linked from the prescription dispensing event. Similar misuse has been experienced with credit card instruments.

In addition to the fraud and abuse issues, monetary incentives for prescription fulfillment have been limited to a uniform value for a particular product offer. For insured patients, pharmaceutical marketers have sought the ability to vary the incentives based upon the individual patient's co-pay amount, which can vary considerably across prescription benefit plans based upon individual patient coverage, cost sharing tiers, drug formulary design, and plan exclusions. To date, no solutions have been identified to address this variability in patient cost-share amounts on a patient-specific basis in real time using the mail-in rebate, debit card or credit card mechanisms.

SUMMARY OF THE INVENTION

In light of the foregoing background, exemplary embodiments of the present invention provide an improved healthcare provider, administrator and method for effectuating a program of the administrator. In addition and in conjunction with the program, exemplary embodiments of the present invention may provide a patient with one or more services. In this regard, when the programs are applied to medications, exemplary embodiments of the present invention may be characterized as a personalized brand medication therapy management, adherence and pharmacosurveillance program that uses data, such as data related to the timing and frequency of prescription fulfillment events (good and/or service purchase events), along with other information in a patient record, to drive personalized, appropriate services for individual patients (clients) enrolled in a program. Exemplary embodiments of the present invention may therefore integrate pharmacy (healthcare provider) adjudication at the point of sale (POS) with services provided during or after the transaction.

In addition to service(s), exemplary embodiments of the present invention may provide a secondary benefit in conjunction with the program, where if monetary, the secondary benefit may offset at least a portion of the out-of-pocket expense for a purchase transaction applicable to the respective program. In such instances, the secondary benefit may be provided in real time at the point of sale in lieu of mailed rebates, ATM debit cards, credit card mechanisms or the like, and may be subject to less risk of fraud or abuse by linking secondary benefit with the dispensing and purchase of a medication. The secondary benefit may also be tied to a patient's actual primary benefit, such as by determining the secondary benefit as a percentage of a primary benefit (further offsetting the cost associated with a purchase transaction). The secondary benefit may also be linked with the patient's compliance to a prescribed therapy that offers additional specificity for the patient's secondary benefit in accordance with predefined business rules based upon individual patient behavior. It should be noted however, that the secondary benefit provided may not include any financial or monetary reward, but instead include other products, services or interventions in accordance with program business rules.

According to one aspect of exemplary embodiments of the present invention, a method is provided that includes initiating adjudication of a primary claim in response to a purchase transaction at a primary payer for a client at a point of sale of a healthcare provider, and adjudicating one or more services of a program of the administrator to which the client is enrolled and/or one or more secondary benefits following the adjudication of the primary claim. The purchase transaction is applicable to the respective program and the respective secondary benefit, and the program includes one or more services. The method also includes providing the one or more services and/or secondary benefits to the client in response to adjudicating the one or more services and/or secondary benefits.

Adjudicating the program service(s) may include receiving an electronic claim transaction submission, such as an electronic claim transaction submission formatted in accordance with the National Council for Prescription Drug Programs (NCPDP) Telecommunication Standard. In such instances, the one or more processing elements may be configured to validate the claim transaction submission prior to providing the at least one of one or more services or one or more secondary benefits to the client.

The secondary benefit may, but need not be a monetary benefit. If the secondary benefit is a monetary benefit, however, the secondary benefit may offset at least a portion of a cost associated with the purchase transaction. In various instances, however, adjudication of the primary benefit may include the primary payer determining a primary benefit offsetting at least a portion of the cost associated with the purchase transaction. And in such instances and when the secondary benefit is a monetary benefit, adjudicating the program service(s) may include determining and providing a monetary secondary benefit further offsetting the cost to the client.

In further instances, the purchase transaction may include a purchase transaction for a good or service. Thus, adjudicating the program service(s) and/or secondary benefit(s) may more particularly include receiving information associated with the purchase transaction for the good or service. The method may then further include maintaining, based on the received information, information regarding historical purchases of the respective good or service, the timing and/or the frequency of the respective historical purchases.

In another embodiment of the present invention, the purchase transaction may be used to verify a client's initial and/or continued eligibility for medication access that may be subject to a Risk Minimization Action Plan (RiskMAP) as a condition of a prescription drug marketing approval by the Food and Drug Administration. And in such instances, program services might also include the collection of relevant laboratory values or other medical information to determine the appropriateness of continued therapy or monitor for adverse effects of the medication. In such instances, program services might also include the provision of an order authorization number to the dispensing provider which is subsequently used to submit patient specific product orders for medications subject to restricted distribution due to product shortages, RiskMAP's or other reasons.

According to other aspects of the present invention, apparatuses (e.g., healthcare provider processing element(s), administrator processing element(s)) and methods are provided. As indicated above and explained below, the healthcare provider, administrator and method for effectuating a program of exemplary embodiments of the present invention may solve the problems identified by prior techniques and may provide additional benefits.

BRIEF DESCRIPTION OF THE DRAWINGS

Figure 1:
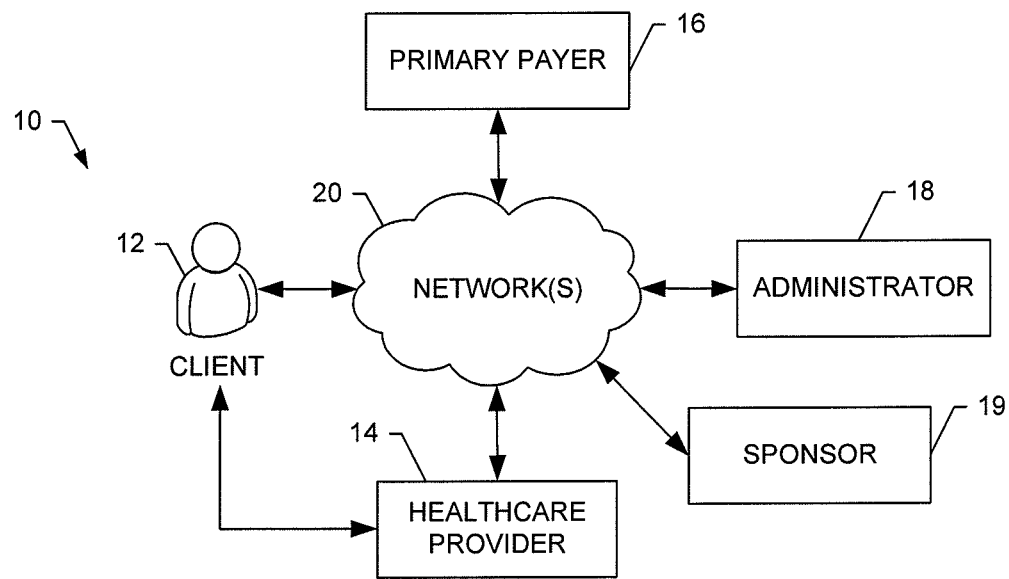
Figure 2:
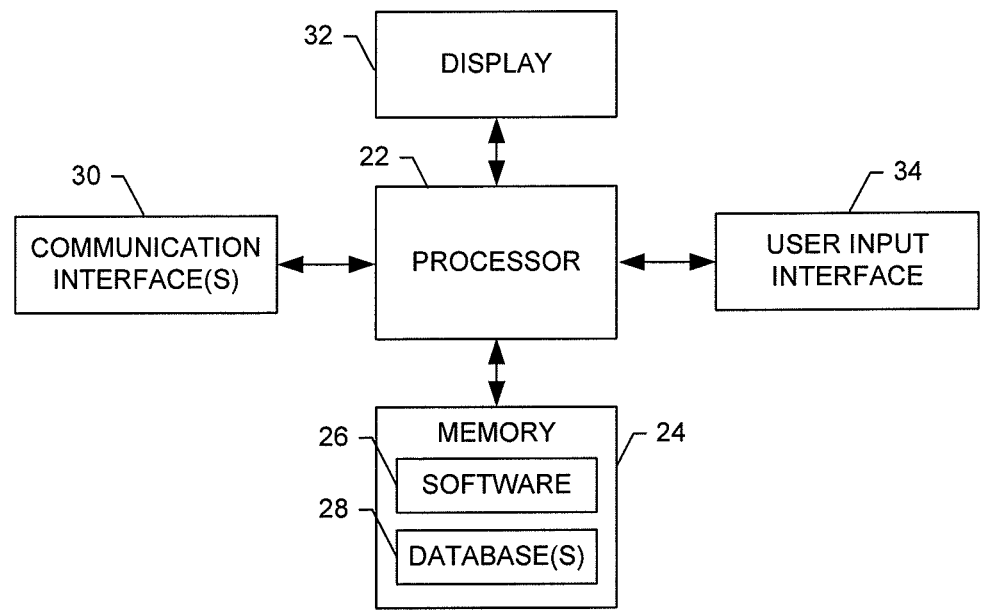
Figure 3:
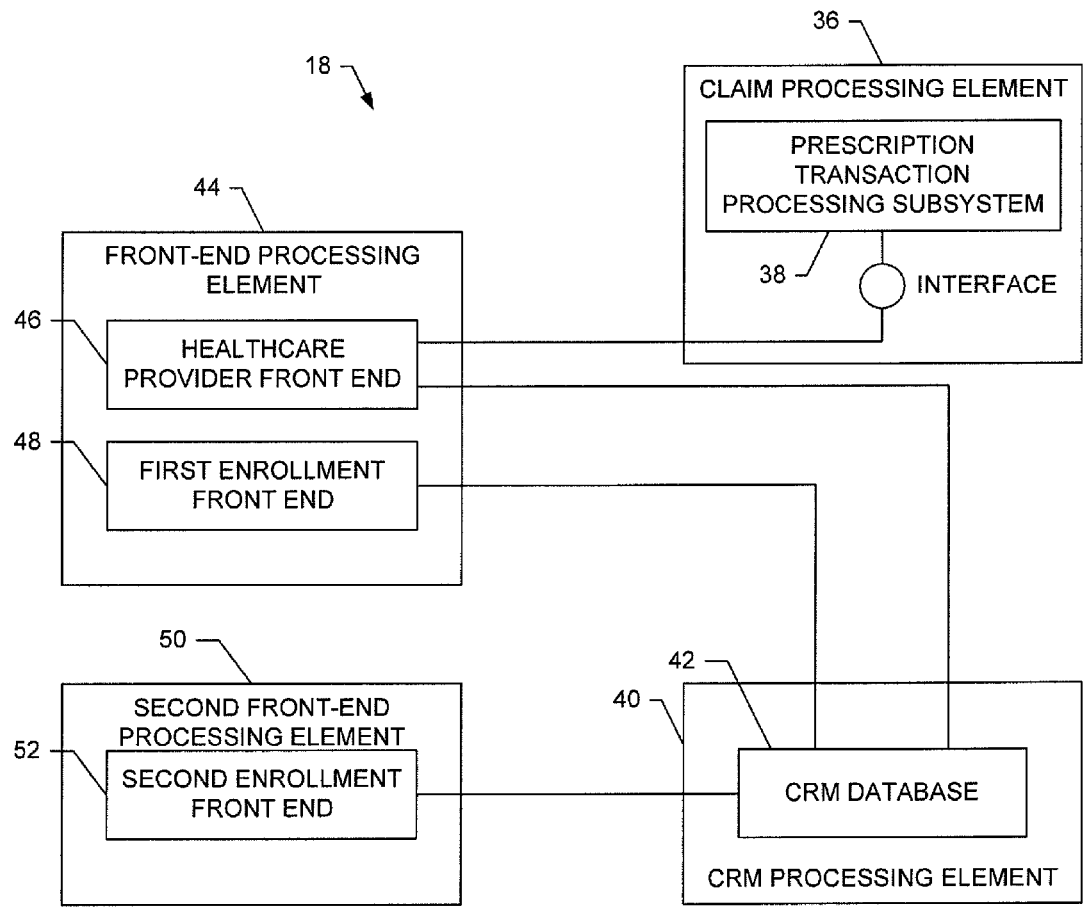
Figure 4:
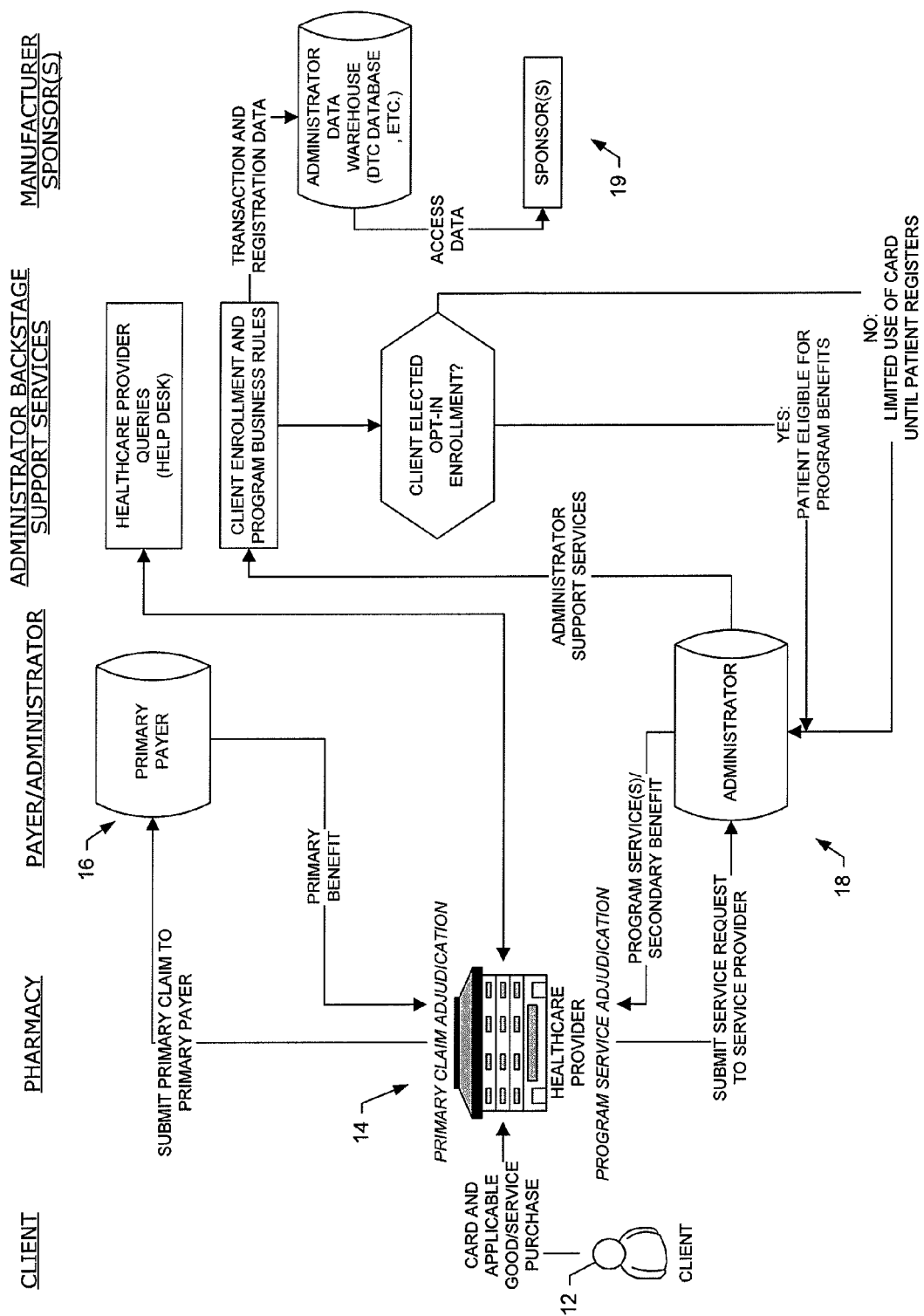
Figure 5:
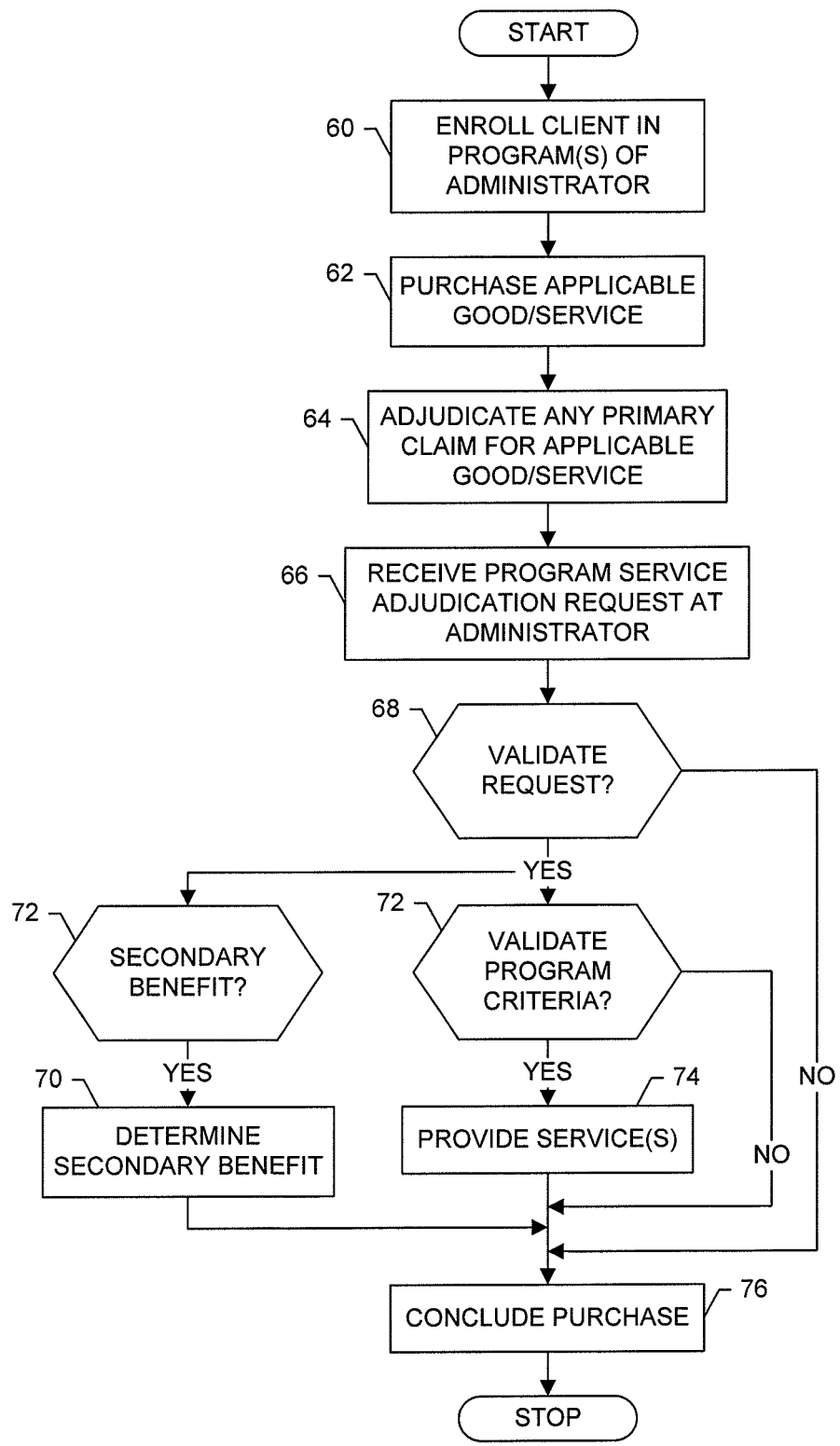

Having thus described the invention in general terms, reference will now be made to the accompanying drawings, which are not necessarily drawn to scale, and wherein:

FIG. 1 is a schematic block diagram of a system for providing a secondary benefit in accordance with exemplary embodiments of the present invention;

FIG. 2 is a schematic block diagram of an entity capable of operating as a client, healthcare provider, primary payer, administrator and/or sponsor, in accordance with embodiments of the present invention;

FIG. 3 is a schematic block diagram more particularly illustrating an administrator, in accordance with one embodiment of the present invention;

FIG. 4 is a control flow diagram of a system performing a method of effectuating a program, such as a medication therapy management, adherence and pharmacosurveillance program, at least partially based on a point of service (POS) transaction, in accordance with exemplary embodiments of the present invention; and FIG. 5 is a flowchart illustrating various steps in a method of effectuating a program, such as a medication therapy management, adherence and pharmacosurveillance program, at least partially based on a POS transaction, in accordance with one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIG. 1, a system 10 for providing a secondary benefit includes one or more clients 12, healthcare providers 14, primary payers 16 and administrators 18 (one of each being shown). Each client 12 is configured to directly and/or indirectly communicate with one or more healthcare providers 14, administrators 18 and/or sponsors 19. Similarly, each healthcare provider is configured to directly and/or indirectly communicate with one or more clients, primary payers 16 and administrators. Each primary payer is configured to directly and/or indirectly communicate with one or more healthcare providers and administrators; and each administrator is configured to directly and/or indirectly communicate with one or more clients, healthcare providers and primary payers. Further, each sponsor is configured to directly and/or indirectly communicate with one or more clients, healthcare providers, primary payers and/or administrators. In this regard, the client(s), healthcare provider(s), primary payer(s), administrator(s) and sponsor(s) can be configured to directly and/or indirectly communicate with one another across one or more networks 20. The network(s) can comprise any of a number of different combinations of one or more different types of networks, including data and/or voice networks. For example, the network(s) can include one or more data networks, such as a local area network (LAN), a metropolitan area network (MAN), and/or a wide area network (WAN) (e.g., Internet), and include one or more voice networks, such as a public-switched telephone network (PSTN). Although not shown, the network(s) may include one or more entities or switches for relaying data, information or the like between the client(s), healthcare provider(s), primary payer(s), administrator(s) and/or sponsor(s).

The client 12, healthcare provider 14, primary payer 16, administrator 18 and sponsor 19 can comprise any one or more of a number of different entities, devices or the like configured to operate in accordance with embodiments of the present invention. In this regard, one or more of the client, healthcare provider, primary payer, administrator and sponsor can comprise, include or be embodied in one or more processing elements, such as one or more of a laptop computer, desktop computer, server computer or the like. Additionally or alternatively, one or more of the client, healthcare provider, primary payer, administrator and sponsor can comprise, include or be embodied in one or more portable electronic devices, such as one or more of a mobile telephone, portable digital assistant (PDA), pager or the like. For example, the client, healthcare provider, primary payer, administrator and/or sponsor can each comprise a processing element configured to communicate with one another across the Internet (e.g., network 20).

It should be understood, however, that one or more of the client 12, healthcare provider 14, primary payer 16, administrator 18 and sponsor 19 can comprise or otherwise be associated with a user carrying out the functions of the respective entity. For example, the client can comprise a client user communicating across a PSTN (e.g., network 20) or in person with an administrator user operating one or more administrator processing elements, where the administrator user and processing element(s) collectively comprise the administrator. Similarly, for example, the client can comprise a client user communicating across a PSTN or in person with a healthcare provider user operating one or more healthcare provider processing elements, where the healthcare provider user and processing element(s) collectively comprise the healthcare provider. In such instances, the primary payers and administrators can comprise one or more respective primary payer and administrator processing elements communicating across a network (e.g., the Internet) with the healthcare provider processing element(s). Alternatively, in such instances, one or both of the primary payers and administrators can comprise a user operating one or more respective processing elements, where the primary payer user and/or administrator user are configured to communicate with the healthcare provider user across a PSTN. As explained below, then, the term client can refer to a client including a client user and/or one or more client processing elements. Similarly, a healthcare provider can refer to a healthcare provider including a healthcare provider user and/or one or more healthcare provider processing elements. A primary payer can refer to a primary payer user and/or one or more primary payer processing elements; and an administrator can refer to a administrator user and/or one or more administrator processing elements. And a sponsor can refer to a sponsor user and/or one or more sponsor processing elements.

Referring now to FIG. 2, a block diagram of an entity configured to operate as a client 12, healthcare provider 14, primary payer 16, administrator 18 and/or sponsor 19 is shown in accordance with exemplary embodiments of the present invention. Although shown as separate entities, in some embodiments, one or more entities may support one or more of a client, healthcare provider, primary payer, administrator and sponsor, logically separated but co-located within the entit(ies). For example, a single entity may support a logically separate, but co-located, primary payer and administrator. Also, for example, a single entity may support a logically separate, but co-located healthcare provider, and primary payer and/or administrator. Further, for example, a single entity may support a logically separate, but co-located administrator and sponsor.

The entity configured to operate as a client 12, healthcare provider 14, primary payer 16, administrator 18 and/or sponsor 19 includes various means for performing one or more functions in accordance with exemplary embodiments of the present invention, including those more particularly shown and described herein. It should be understood, however, that one or more of the entities may include alternative means for performing one or more like functions, without departing from the spirit and scope of the present invention. More particularly, for example, as shown in FIG. 2, the entity can include a processor 22 connected to a memory 24. The memory can comprise volatile and/or non-volatile memory, and typically stores content, data or the like. In this regard, the memory may store software applications 26, instructions or the like for the processor to perform steps associated with operation of the entity in accordance with embodiments of the present invention. The memory may also store content transmitted from, and/or received by, the entity. In this regard, when the entity comprises a primary payer or an administrator, the memory may store one or more databases 28 for administering programs offered thereby, such as by storing information identifying or otherwise associated with clients, or more particularly client users, enrolled in those programs, as explained below. As described herein, the software application(s) may each comprise software operated by the respective entities. It should be understood, however, that any one or more of the client applications described herein can alternatively comprise firmware or hardware, without departing from the spirit and scope of the present invention.

In addition to the memory 24, the processor 22 can also be connected to at least one interface or other means for displaying, transmitting and/or receiving data, content or the like. In this regard, the interface(s) can include at least one communication interface 30 or other means for transmitting and/or receiving data, content or the like. In addition to the communication interface(s), the interface(s) can also include at least one user interface that can include one or more earphones and/or speakers, a display 32, and/or a user input interface 34. The user input interface, in turn, can comprise any of a number of devices allowing the entity to receive data from a user, such as a microphone, a keypad, a touch display, a joystick, or other input device.

Reference is now made to FIG. 3, which more particularly illustrates an administrator 18 in accordance with exemplary embodiments of the present invention. As shown in FIG. 3, the administrator includes a plurality of processing elements. It should be understood that each processing element may include a processor, memory, communication interface(s), display and/or user input interface(s), such as in the same manner explained above with reference to FIG. 2. It should also be understood that, although shown as separate entities, in some embodiments, more than one of the illustrated processing elements may be supported by a single processing element, without departing from the spirit and scope of the present invention.

As shown in FIG. 3, the administrator 18 of exemplary embodiments of the present invention includes a claim processing element 36 configured to operate a prescription transaction processing subsystem 38 for processing benefits to clients 12 enrolled in one or more programs offered by the administrator. In this regard, the prescription transaction processing subsystem may comprise a software package based on a claims processing system, such as the ProPBM™ prescription transaction processing system distributed by Prospective Health Services of Scottsdale, Ariz. The prescription transaction processing subsystem may capture and/or adjudicate prescription transactions for potential benefits, interventions or other services provided under one or more programs offered by the administrator based on one or more business rules and/or attributes applicable to the respective program(s). One or more of the programs offered by the administrator may have an associated sponsor 19, such as the manufacturer of a product or service to which the program(s) are directed. As such, the prescription transaction processing subsystem may utilize relational database technology and advanced logic to assign multiple identification numbers to a client enrolled to participate in multiple programs offered by the administrator. Thus, to receive services (and, if so desired, benefits) under multiple programs of the administrator, as explained below, the client user may be issued a membership card tied to multiple programs from different manufacturers. The membership card, then, may include among other pieces of information, an identifier (client identification number) and/or source code associated with the respective client, and/or one or more identifiers (program identification numbers) associated with programs of the administrator to which the respective client is enrolled.

As shown, the administrator 18 may also include a Customer Relationship Management (CRM) processing element 40 for enrolling clients 12 in one or more programs of the administrator, as well as providing one or more services to clients enrolled in program(s) of the administrator. The CRM processing element may maintain a CRM database 42 for storing information associated with the program(s) and the clients enrolled in those program(s). The client information maintained in the CRM database may include, for example, demographic information such as the client's name, address, telephone number, e-mail address, and the like. The client information may include the aforementioned client identification number and/or source code associated with the respective client, which may be included on a membership card issued to the client. In addition, the client information may include a listing of one or more program(s) of the administrator to which the client is enrolled (or program identification number(s) of such program(s)), one or more goods and/or services to which the client's enrolled program(s) are applicable, any particular services and/or benefits associated with respective applicable goods/services, historical purchases of applicable goods and/or services, the timing and/or frequency of those historical purchases, any scheduled forthcoming purchases of applicable goods and/or services, or the like.

The administrator 18 further includes one or more front-end processing elements for interfacing clients 12 and healthcare providers 14 with the administrator. More particularly, for example, the administrator can include a front-end processing element 44 that includes a healthcare provider front end 46, such as a software application front end, for interfacing a healthcare provider with the prescription transaction processing subsystem 38 of the claim processing element 36. In this manner, the healthcare provider may initiate effectuation of a program for which a client purchasing a good and/or service is enrolled (as determinable based on client information maintained in the CRM database 42). The front-end processing element may include a first enrollment front end 48 for enrolling clients in one or more programs of the administrator. The first enrollment front end may enroll clients in any of a number of different manners. And as such, the administrator may include further front-end processing elements, including the shown second front-end processing element 50 having a second enrollment front end 52 for enrolling clients. In one embodiment, for example, the first enrollment front end may comprise an interactive voice response (IVR) system configured to communicate with the client via voice commands across a voice network 20 (e.g., PSTN), and configured to communicate with the CRM processing element 40, and hence the CRM database, via data commands across a data network (e.g., the Internet). The second enrollment front end, then, may comprise an application server configured to present a graphical user interface (GUI) via which a client, or other party under direction of the client (e.g., customer service representative—CSR—of the administrator) interact with the CRM processing element.

As shown and described herein without loss of generality, the clients 12, healthcare providers 14 and primary payers 16 may comprise or otherwise be associated with patients, pharmacies providing prescription medication to those patients, and insurance companies providing an insurance benefit or coverage (primary benefit) to those patients. It should be understood, however, that the clients, healthcare providers and primary payers may comprise or otherwise be associated with any of a number of other entities equally configured to perform the functions described herein. For example, the healthcare providers can comprise any of a number of different entities configured to provide goods and/or services to customers, those goods and/or services being for which a primary payer is configured to provide a primary benefit, and for which an administrator 18 is configured to effectuate a program, as explained below.

As explained in the background section, for a number of years, pharmaceutical manufacturers have provided patients with personalized marketing services and programs including rebates, point-of-sale free product samples, ATM gift cards, educational mailings and medication refill reminders, in order to encourage product adoption or promote the continued use of their brand medications. Independent-marketing service providers not associated with a particular third-party payer (e.g., insurance company) or pharmacy, however, have been limited by their inability to link marketing services with prescription fulfillment activity for patients within a cross-section of pharmacies, PBMs or health plans. Also, for a number of years pharmaceutical companies have followed trends from other consumer markets by providing financial incentives in the form of debit "gift" cards or credit card mechanisms. Such incentives, however, have not been linked to the fulfillment of the associated prescription, and in many cases consumers have used the cards in ways not intended by their issuers.

Exemplary embodiments of the present invention therefore provide an architecture for effectuating one or more programs at least partially based on point-of-sale (POS) transactions. In addition and in conjunction with such programs, the architecture of exemplary embodiments of the present invention may provide a patient (client 12) with one or more services and/or secondary benefits from a sponsor 19 of a program offered by a administrator 18, which may cover a portion of the out-of-pocket expense for applicable medications (qualifying goods and/or services). Each of these aforementioned features being briefly explained below before being explained in detail thereafter.

A. Managing Product Services

The architecture of exemplary embodiments of the present invention may be characterized as a personalized medication therapy management, adherence, loyalty and pharmacosurveillance program that uses data, such as data related to the timing and frequency of prescription fulfillment events (good and/or service purchase events), along with other information in an electronic prescription claim transaction submission record, to drive appropriate services for individual patients (clients 12) enrolled in a program. The architecture may therefore integrate pharmacy (healthcare provider 14) adjudication at the point of sale (POS) with services provided during or after the transaction. Prescription fulfillment activity, demographics, and other information for patients who opt-in to a program offered by the administrator 18 may be available thereto in any of a number of different ways, such as via a connection of the administrator to pharmacies (healthcare providers) using the coordination of benefits (COB) segment of an electronic claim transaction submission formatted in accordance with the National Council for Prescription Drug Programs (NCPDP) Telecommunication Standard Version 5.1 (hereinafter "NCPDP v5.1"). Based on business rules established by an entity, such as the administrator or a sponsor 19 of a program offered by the administrator, the administrator may link an event-based consumer management system with a network of participating pharmacies to capture patient pharmacy prescription transactions for a brand medication along with other information in a patient record. This data, then, may "trigger" specified consumer services such as marketing services and/or interventions for the patients including, for example, refill reminders, reimbursement counseling services, clinical monitoring or counseling services, ATM gift cards, textbooks, educational mailings, or other activities to address specific drug and disease state issues or opportunities.

Providing the underlying data architecture in various instances, NCPDP v5.1 may allow independent service providers (e.g., administrator 18, sponsor 19, etc.), which process electronic prescription transactions from a network of one or more pharmacies (healthcare providers 14), expanded visibility into those pharmacies' prescription records for enrolled clients. The visibility extends to client prescription history that may exist across multiple claim processors, across multiple healthcare providers, across multiple medications, and/or for therapies prescribed across multiple physicians. Thus, not only may a service provider access a patient prescription transaction they have processed, the service provider may also access prescription transactions for the same patient and product processed by other entities. Such a comprehensive cross-sectional view into patient-specific medication-dispensing records may be captured through utilization of the COB segment of NCPDP v5.1, which was established for prescription claim processing. Although designed to accommodate additional payer levels in conjunction with coordination of prescription benefits under multiple payers, this new functionality offers a one-to-two (or more if necessary) relationship between a dispensing transaction event and both the third party payer (e.g., primary payer 16, etc.) and the administrator or sponsor of the medication therapy, adherence and pharmacosurveillance program.

The architecture of exemplary embodiments of the present invention may also permit an entity, such as the administrator 18 or sponsor 19 of a program offered by the administrator, to review and analyze the impact of services provided to patients (i.e., enrollees) enrolled in a program of the administrator. In this regard, the architecture may integrate subsequent prescription utilization data with information captured through the provision of services under the program of the administrator to measure changes in program compliance, product adherence, adverse events, therapeutic outcomes or the like, and may also trigger additional service events in response to each patient's individual program, service or product experience.

As referenced in the above context, the architecture of exemplary embodiments of the present invention may manage (or facilitate managing) programs providing non-marketing services including Phase IV clinical trial surveillance, FDA-mandated risk minimization action plans (RiskMAP's), controlled distribution services for limited-supply products, patient assistance programs (PAPs) and the like. These programs typically use proprietary databases linked to pharmacies (healthcare providers 14) to authorize and capture prescription fulfillment event data (via separate transactions) and trigger other patient or product management events. Using the architecture of exemplary embodiments of the present invention in lieu of the foregoing, any prescription authorization, tracking or management event triggering could occur at the same time the pharmacist adjudicates the prescription for third-party reimbursement. Further, by initially opting-in to a particular program of the administrator 18, such as for a particular brand of medication, a patient may also permit the administrator to enroll the patient in additional programs offered by the administrator, such as for other brands of medications. This enables the administrator to offer sponsors 19 streamlined access to willing patients, thus avoiding the marketing, card production, and enrollment processing costs associated with each new program participant.

As briefly mentioned above, embodiments of the present invention may be used to administer an FDA mandated risk minimization action plan (Risk MAP) for a newly approved drug product, or for an existing product which warrants closer monitoring due to the emergence of product safety signals after product launch and broader patient use. In one example of this embodiment, both patient and pharmacy access to the product could be tightly controlled to facilitate its safe and appropriate use. Although some current programs incorporate paper stickers to authorize product dispensing, embodiments of the present invention allow deployment of computerized, real-time transaction authorization, management and tracking in accordance with defined, systematic business rules that determine program eligibility and product access. For such a controlled access product, physicians may use the card as a product eligibility vehicle. Patients may be required to complete an enrollment process which may subsequently activate the card. The patient may present the card and prescription for the controlled access product to the pharmacist. After completing the insurance claim adjudication process, a secondary claim may be routed to the program administrator, which electronically verifies and confirms patient eligibility and automatically arranges for shipment of the product to the dispensing pharmacy.

In another embodiment, the system generated data could be used to coordinate structured clinical interventions and patient level medication therapy management services. For example, for patients who are prescribed a specialty injectable medication, the physician could provide patients with an enrollment card which, when activated and used at the point of sale, could trigger an outbound call to the patient to provide the assistance and training necessary to teach patients how to reconstitute lyophilized product, how to self-inject the medication, manage side effects, and monitor for potential adverse reactions. The patient may present the card to the pharmacist, which provides the necessary instructions for transmission of the secondary transaction. By linking the clinical interventions to specific dispensing events captured by the system, a series of timely and rational interventions may be scheduled in accordance with the individual characteristics of the drug and disease state being treated B. Secondary Benefits Provided by Administrator In addition to or in lieu of managing various product services for pharmaceutical manufacturers, the architecture of exemplary embodiments of the present invention may provide patients (clients 12) with a seamless, secondary benefit such as a financial incentive covering a portion of an out-of-pocket expense for medications to which the client's enrolled programs are applicable (applicable goods and/or services), although it should be understood that such a secondary benefit need not be monetary. In those instances in which the benefit is a financial incentive, however, the otherwise out-of-pocket expense may be determined by the administrator in any of a number of different ways, such as via a connection of the administrator to pharmacies (healthcare providers) using the aforementioned COB segment of a NCPDP v5.1-formatted claim transaction submission, the COB segment including a secondary payer field. The secondary benefit may be provided in lieu of mailed rebates, ATM debit cards, credit card mechanisms or the like, and may be subject to less risk of fraud or abuse when the secondary benefit is tied to the purchase of a medication. The secondary benefit may also be tied to a patient's actual primary benefit, such as by determining the secondary benefit as a percentage of a primary benefit. For example, the secondary benefit may be tied to, and calculated as a percentage of, the co-pay of a prescription plan, thereby providing flexibility to address the needs of an individual relative to their prescription coverage.

For example, according to one embodiment of the present invention, a program could be designed to capture the patient's cost share requirement for a drug as determined by the patient's prescription drug coverage and subsequently provide the patient an additional discount on the final prescription cost. This additional discount amount could be calculated instantly and provided to the patient at the point of sale and dispensing. By using the databases, software, and business rules defined by the processor and transmitted via networks to the pharmacy provider, this discount could be defined and structured in a variety of ways to address individual patient, product, and cost issues. Although fixed discounts may be offered, such as a flat $5.00 discount, other techniques may be used, such as variable discounts which reduce all patient cost share amounts, regardless of individual drug benefit coverage, to a fixed dollar amount. Alternatively, percentage discounts may be useful in certain circumstances (e.g., reduce patient calculated cost share by 15%). In other instances, the manufacturer may deploy a program which combines certain aspects of these options to create additional discount calculation options.

According to a further aspect of the present invention, a patient may be provided a service and a secondary benefit. For instance, a pharmaceutical manufacturer may provide physicians with patient enrollment kits, which might include drug product information, disease information or other relevant references or materials deemed of potential value to newly prescribed patients for a given manufacturer's product. For example, the information may include tips on healthy eating habits to help manage cholesterol levels. Included within these patient kits, the manufacturer may also include a card which, upon activation, the patient may utilize to receive a discounted cost share for the prescription at their local pharmacy. The patient could activate the card using one of multiple program interfaces such as the internet, interactive voice response, facsimile, or by calling a toll free customer service number. After completing the activation process, the patient could present the card to the pharmacist, along with any other prescription drug coverage card (subject to certain exclusions required by law such as Medicare and Medicaid). When filling the prescription, the pharmacy may input specific data elements provided on the card into the patient's associated secondary coverage fields within the pharmacy computer system. The pharmacist may then fill the prescription and electronically submit the prescription claim to the patient's insurance company or pharmacy benefit manager (PBM). However, after the prescription claim response is received by the pharmacy from the patient's insurance company or PBM, a secondary transaction may be subsequently and automatically submitted in accordance with the manufacturer card program, and a secondary transaction response may be received by the pharmacy.

Implementing the aforementioned features, the architecture of exemplary embodiments of the present invention may incorporate the use by service providers of fields, including a secondary payer field of the COB segment of a NCPDP v5.1-formatted claim transaction submission to the administrator 18. Such a transaction submission may trigger the administrator to provide services under one or more programs, which may include providing a secondary benefit that, if monetary, may offset at least a portion of a co-pay due from a patient (client 12) with coverage (i.e., primary benefit) from an insurance company (primary payer 16). In such instances, once the pharmacy has entered into their pharmacy management systems in the appropriate secondary payer field, an eligible program identification number from a membership card of the patient, the architecture may automatically adjudicate program transaction information and subsequently provide services that may include a co-pay offset from the primary benefit upon prescription fulfillment and in accordance with one or more program business rules. These business rules may specify, for example, a fixed incentive, or a variable incentive applied toward a patient's individual out-of-pocket responsibility. In either instance, the patient may not be required to perform any task other than fill the prescription to realize the secondary benefit.

If the patient is cash-paying or is otherwise unable to realize a primary benefit from a primary payer 16, the architecture of exemplary embodiments of the present invention may process the same automatic adjudication for a cost offset, such as by capturing the aforementioned program identification number in a primary payer field of a NCPDP v5.1-formatted claim transaction submission. At the conclusion of a transaction in either instance (primary and secondary benefits, or only a secondary benefit—effectively in this instance a primary benefit), the administrator 18 may provide a real-time response to the pharmacy (healthcare provider 14), such as in the NCPDP v5.1 format, to communicate one or more services and any secondary benefit provided to the patient and the accounts payable information for the pharmacy.

Reference is now made to FIGS. 4 and 5, which illustrate a control flow diagram and a flowchart including various steps in a method of effectuating a program at least partially based on point-of-sale transactions in accordance with exemplary embodiments of the present invention. As shown at block 60 of FIG. 5, the method of one exemplary embodiment includes enrolling a client 12 with one or more programs offered by a administrator 18, one or more of which may include an associated sponsor 19. The client may directly or indirectly enroll with program(s) of the administrator in any of a number of different manners. For example, as shown in FIG. 4, the client may enroll with one or more program(s) via a healthcare provider 14 during the purchase of a good/service to which the respective program(s) is applicable. Additionally or alternatively, for example, the client may enroll with one or more program(s) independent of a healthcare provider before the purchase of an applicable good/service. In either instance, however, at or before enrolling in the program(s), the client may be presented with a membership card including, among other pieces of information, an identifier (client identification number) and/or source code associated with the respective client, and/or one or more identifiers (program identification numbers) associated with the respective program(s). The membership card may then be used for real-time program eligibility verification and transaction processing. The membership card need not be associated with any debit or credit card processes, although it should be realized that the membership card may be integrated with one or more of these funded account programs, if so desired.

More particularly, for example, enrolling in one or more programs of a administrator 18 may include a client 12 initiating contact with the administrator, such as via the first enrollment front end 48 (e.g., IVR) of the front-end processing element 44, or via the second enrollment front end 52 (e.g., CSR) of the second front-end processing element 50. After initiating contact with the administrator, the client may send and the administrator may receive one or more pieces of information regarding the client and/or program(s) to which the client desires to enroll. In this regard, the client information may include, for example, demographic information such as the client's name, address, telephone number, e-mail address, and the like, a client identification number and/or source code associated with the respective client. Also, the client information may include, for example, a listing (or program identification numbers) of one or more programs of the administrator to which the client is enrolled, one or more goods and/or services to which the client's enrolled program(s) are applicable. In addition, client information may include, for example, unique program enrollment and/or ongoing eligibility requirements such as physician authorization or attestations, laboratory data, client attestations or the like. Further, for example, the client information may include any particular services and/or benefits associated with respective applicable goods/services, historical purchases of applicable goods and/or services, the timing and/or frequency of those historical purchases, any scheduled forthcoming purchases of applicable goods and/or services, or the like.

After receiving the client information, the administrator, or more particularly the CRM processing element 40 of the administrator, may attempt to validate some or all of the received information, such as by validating that the received information is complete or sufficient to proceed, and/or validating that the information does not violate any logic rules. If the administrator fails to validate the appropriate information, the administrator may deny enrollment. Alternatively, provided the administrator includes multiple enrollment front ends, the administrator may attempt to enroll the client via another front end. For example, the administrator may attempt to enroll the client via the second enrollment front end (e.g., CSR), if the administrator fails to enroll the client via the first enrollment front end (e.g., IVR).

In addition to validating the client information, the administrator 18, or more particularly the CRM processing element 40 of the administrator, may attempt to validate the client's eligibility to enroll in the desired program(s) of the administrator. This validation may include, for example, validating or otherwise verifying that the client's eligibility based on whether the client is or is not enrolled in Medicaid or Medicare (and if so, the administrator 18 may require further information—e.g., client financial information—to validate the client's eligibility for a patient assistance program). Additionally or alternatively, for example, the CRM processing element may attempt to validate or otherwise verify the client's eligibility based on the client's state of residence (or where the client is otherwise located), which may be subject to laws precluding certain programs or services. Similar to validating the client information, if the administrator fails to validate the client's eligibility, the administrator may deny initial enrollment or terminate ongoing enrollment. If the administrator successfully validates the client information and the client's eligibility, however, the administrator may enroll the client 12 in the respective program(s) of the administrator, including storing and maintaining client information in the CRM database 42 of the CRM processing element of the administrator. The client information maintained in the CRM database may include, for example, the aforementioned client information received by the client, which during the client's enrollment in the respective program(s) may be updated or otherwise modified, such as to track historical purchases of qualifying goods and/or services, the timing and/or frequency of those historical purchases, ongoing client information required for continued program eligibility, or the like.

Irrespective of exactly how the client 12 is enrolled with one or more programs of the administrator 16, the client may thereafter be eligible to receive one or more services and, in conjunction with such services (if so established in accordance with program business rules) a secondary benefit for goods/services to which the respective program(s) is applicable. As shown in FIG. 4, however, the client may be required to opt-in to a program before receiving some of the service(s) and/or benefit(s) of a program. In such instances, the client may activate their membership card to receive some service(s) and/or benefit(s) of a program, such as by receiving a service and/or benefit with a limited purchase or time enrollment with the program. The client may then be required to separately opt-in to the program long term to continue to receive those service(s) and/or program(s), and/or to receive additional service(s) and/or program(s). According to another aspect, the program could be structured to allow patients to opt-in to the program and qualify for additional prescription discounts when refilling the prescription. As an alternative to traditional discount programs which offer a standard discount amount, the system could incorporate business rules which provide greater discounts or more frequent discounts to compliant patients that are refilling their prescriptions in accordance with their physician's prescribed instructions.

As indicated above, the services of the program may be received in addition to any applicable primary benefit for such goods/services, if appropriate. In this regard, after enrolling the client, the method includes the client purchasing an applicable good/service from a healthcare provider 14, as shown in block 62 of FIG. 5, or in other words the healthcare provider effectuating a purchase transaction for the client. The respective purchase may be effectuated in any of a number of different manners such as, for example, by presenting a qualifying good/service (or identifier of such a good/service) and a membership card (or client identification number and/or source code otherwise printed on such a card) for the program to a healthcare provider 14 at the point of service (POS).

As or after the client 12 purchases a qualifying good/service from a healthcare provider 14, adjudication of a primary claim with a primary payer 16 may be effectuated to thereby determine any applicable primary benefit (e.g., prescription drug benefit) coverage offsetting a portion of the cost of the respective good/service paid by the client to the healthcare provider, as shown in block 64. Similarly, one or more services of one or more programs may be adjudicated with an administrator 18 to thereby determine one or more services to provide to the client, and/or to determine a secondary benefit that, if monetary, may further offset a portion of the cost of the respective good/service paid by the client to the healthcare provider, as explained in further detail below with respect to blocks 66-76. Adjudication of the primary claim and program service(s) may be initiated in any of a number of different manners. In one exemplary embodiment, for example, the adjudications are initiated by the healthcare provider submitting an electronic NCPDP v5.1-formatted claim transaction to the primary payer and the administrator. In such instances, the claim transaction submission may include information identifying the primary payer in a primary payer field, and identifying the administrator in a secondary payer field of a COB segment. In addition, the adjudications may occur sequentially, such that adjudication at the primary payer occurs prior to adjudication at the administrator. In this instance, the primary payer may not be included or identifiable where the secondary payer receives the claim transaction submission after being adjudicated by the primary payer. Moreover, the claim transaction submission may include a number of other pieces of information as desired or necessary, such as, for example, information identifying the client, the applicable good/service, a program of the primary payer to which the client is enrolled (e.g., insurance program), and/or a program of the administrator to which the client is enrolled.

More particularly as to adjudication of the program service(s), the administrator 18 may receive a request for program service adjudication from the healthcare provider 14, such as by receiving the electronic NCPDP v5.1-formatted claim transaction submission into the prescription transaction processing subsystem 38 of the claim processing element 36 of the administrator, as shown in block 66. After receiving the claim transaction submission including any required client and/or purchase information, the prescription transaction processing subsystem may attempt to validate the submission, as shown in block 68. The prescription transaction processing subsystem can attempt to validate the submission in any of a number of different manners, including by attempting to validate that the client 12 is enrolled in a program of the administrator, verifying that client is currently eligible for the program, and that the respective program is applicable to the purchased good/service. Irrespective of how the submission is validated, if the prescription transaction processing subsystem fails to validate the submission, the administrator may deny adjudication of the program service(s). If the prescription transaction processing subsystem successfully validates the claim transaction submission, however, the prescription transaction processing subsystem 38 may extract one or more pieces of information included in the submission, and pass that information to the CRM processing element 40. In addition, the prescription transaction processing subsystem may pass additional information that may or may not have been included in the claim transaction submission such as, for example, the date and/or time of purchase. At least some of this information may then be stored in the CRM database 42 along with other pieces of client information, such as to maintain, for the client, information regarding historical purchases of qualifying goods and/or services, the timing and/or frequency of those historical purchases, and the like. The information may be used at one or more instances for a number of different purposes, such as for analysis by one or more sponsor(s) 19 of the program(s) of the administrator, as shown in FIG. 4.

In addition to or in lieu of storing information in the CRM database 42, at least some of the information extracted and passed to the CRM processing element 40 may be utilized to identify one or more, if any, services to provide to the client under the respective program of the administrator. After receiving the information, then, the CRM processing element may validate the criteria for providing services under the respective program based on one or more business rules associated with the program, as shown in block 70. In this regard, the CRM processing element may validate the criteria to determine any services to provide to the client 12 by virtue of the client's enrollment and/or continued eligibility in a program of the administrator, and the client's purchase of applicable good/service under the program. These services may include consumer marketing services and/or interventions for the patients including, for example, refill reminders, reimbursement counseling services, clinical counseling services, ATM gift cards, textbooks, educational mailings, or other activities (e.g., professional assistance, such as by phone) to address specific drug products, disease state adherence issues or other issues and opportunities. Irrespective of the exact services that may be provided to the client, after determining the appropriate service(s), the CRM processing element may provide, or otherwise facilitate providing, those service(s) to the client, as shown in block 72.

Also after successfully validating the claim transaction submission, the prescription transaction processing subsystem may determine if any secondary benefit applies to the respective good/service and, if so, calculate or otherwise determine a secondary benefit that, if monetary, may further offset a portion of the cost of the respective good/service or other program services, as shown in blocks 74 and 76. The secondary benefit may be determined independent of or otherwise without regard to any applicable primary benefit provided by the primary payer 16. Alternatively, as indicated above, the secondary benefit may be determined based on the primary benefit, such as a monetary benefit calculated by determining a percentage (e.g., co-pay offset) of the primary benefit. In such instances, the prescription transaction processing subsystem may be informed of the certain data associated with the primary benefit, such as data from the primary payer, healthcare provider or another entity.

Before and/or after the administrator 18 provides one or more services to the client 12, and after the administrator determines any secondary benefit, the client may conclude the purchase of the appropriate good/service that triggered the secondary benefit and services, as shown in block 76. The client may conclude the purchase with the healthcare provider 14 based on the primary benefit as determined by the primary payer 16 and any secondary benefit determined by the administrator. In such instances, the primary payer and administrators may notify the healthcare provider of the primary and secondary benefits, such as by notifying the healthcare provider of a final cost or price of the purchased good/service to be charged to the client (the cost/price of the purchased good/service reduced by the sum of the primary and secondary benefits). The client may then remit the final cost or price to the healthcare provider. The healthcare provider may, during the purchase transaction or a later time, receive the primary and secondary benefits from the primary payer and administrator. Alternatively, the primary payer and administrators may provide the client with the primary and secondary benefits during or after the transaction. In these instances, the client may be directed to remit the entire cost of the purchased good/service to the healthcare provider. The primary payer and administrators may also provide the healthcare provider with other information related to the primary and secondary benefits, such as an order authorization numbers to secure product inventory, program ineligibility or the like.

As will be appreciated, the method of effectuating a program, including at least those steps shown at blocks 62-78, may be repeated a number of different instances during the client's enrollment in a program of the administrator 18. Thus, at one or more instances, the client 12 may purchase, from a healthcare provider 14, one or more goods/services to which an enrolled program of the administrator is applicable. Triggered by such purchases, then, the primary payer and administrator may determine primary and secondary benefits which may also include reducing the cost paid by the client for the respective goods/services. In addition, the administrator may determine one or more services to provide to the client's purchase of an applicable good/service under the respective program (and the client's enrollment in the program).

According to one aspect of the present invention, all or a portion of the system of the present invention, such as all or portions of the client 12, healthcare provider 14, primary payer 16, administrator 18 and/or sponsor 19, generally operates under control of a computer program product. The computer program product for performing the methods of embodiments of the present invention includes a computer-readable storage medium, such as the non-volatile storage medium, and computer-readable program code portions, such as a series of computer instructions, embodied in the computer-readable storage medium.

In this regard, FIGS. 4 and 5 are a control flow diagram and flowchart of methods, systems and program products according to the invention. It will be understood that each block or step of the control flow diagram and flowchart, and combinations of blocks in the control flow diagram and flowchart, can be implemented by computer program instructions. These computer program instructions may be loaded onto a computer or other programmable apparatus to produce a machine, such that the instructions which execute on the computer or other programmable apparatus create means for implementing the functions specified in the block(s) or step(s) of the control flow diagram and flowchart. These computer program instructions may also be stored in a computer-readable memory that can direct a computer or other programmable apparatus to function in a particular manner, such that the instructions stored in the computer-readable memory produce an article of manufacture including instruction means which implement the function specified in the block(s) or step(s) of the control flow diagram and flowchart. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block(s) or step(s) of the control flow diagram and flowchart.

Accordingly, blocks or steps of the control flow diagrams support combinations of means for performing the specified functions, combinations of steps for performing the specified functions and program instruction means for performing the specified functions. It will also be understood that each block or step of the control flow diagram and flowchart, and combinations of blocks or steps in the control flow diagram and flowchart, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. For example, a client may enroll in a program and obtain a membership card instructing healthcare providers to send a program adjudication request (or primary if the client is not enrolled in a program of a primary payer) to the administrator at the POS. In response, the administrator may screen the respective applicable good/service against similar goods/services for relevant comparisons. For example, the administrator could screen an appropriate medication against other medications for the same client and, if so desired, other applicable clinical and drug information provided by the client during program enrollment for potential drug interactions, therapeutic overlap or the like. In the context of providing medications, pharmacies (healthcare providers) may screen for such information, but patients (clients) often use multiple pharmacies. PBMs (Pharmacy Benefits Managers) may screen for this, but PBMs do not always cover the medication, and therefore may not have access to all prescription drug information. Other patients may not have a prescription benefit and the drug interaction screening that a PBM would provide. The architecture of this aspect of exemplary embodiments of the present invention, if deployed in this manner, may transcend such limitations by being specific for that patient. The administrator could deploy this to provide comprehensive drug information for the provision of patient specific medication therapy management (MTM) programs, such as those mandated for Medicare Part D beneficiaries as a result of the Medicare Modernization Act (MMA).

It should therefore be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising one or more processors and one or more memories storing executable instructions that in response to execution by the one or more processors cause the apparatus to at least:
   receive an electronic claim transaction submission at an administrator in response to a purchase transaction of a client at a point of sale of a healthcare provider, a primary payer separate and distinct from the administrator also receiving the electronic claim transaction submission from the healthcare provider to initiate adjudication of a primary claim for an offset of at least a portion of a cost associated with the purchase transaction; and
   adjudicate, in response to receiving the electronic claim transaction submission at the administrator and separate and distinct from adjudication of the primary claim by the primary payer, one or more services of a program of the administrator to which the client is enrolled, the purchase transaction being applicable to the program, the one or more services including one or more marketing services or interventions;
   wherein the one or more processors also trigger provision of the one or more services to the client in response to adjudication of the one or more services.

2. The apparatus of claim 1, wherein the apparatus is caused to receive the claim transaction submission formatted in accordance with the National Council for Prescription Drug Programs (NCPDP) Telecommunication Standard.

3. The apparatus of claim 1, wherein the one or more memories store further executable instructions that in response to execution by the one or more processors cause the apparatus to further extract one or more items associated with the claim transaction submission in order to trigger provision of one or more additional services to the client.

4. The apparatus of claim 1, wherein the apparatus being caused to adjudicate the one or more services includes being caused to further adjudicate one or more secondary benefits, the purchase transaction being applicable to the program and the one or more secondary benefits, and wherein the apparatus being caused to trigger provision of the one or more services includes being caused to further trigger provision of the one or more secondary benefits to the client in response to adjudication of the one or more secondary benefits.

5. The apparatus of claim 4, wherein the primary payer has received the electronic claim transaction submission to enable the primary payer to determine a primary benefit offsetting at least a portion of the cost associated with the purchase transaction, and wherein the apparatus being caused to adjudicate the one or more secondary benefits includes being caused to determine a monetary secondary benefit further offsetting the cost, the secondary benefit being provided through the administrator.

6. The apparatus of claim 1, wherein the purchase transaction comprises a purchase transaction for a good or service, and wherein the apparatus being caused to adjudicate the one or more services includes being caused to receive information associated with the purchase transaction for the good or service, and maintain, based on the received information, information regarding one or more of historical purchases of the good or service, a timing or a frequency of the historical purchases.

7. An apparatus comprising one or more processors and one or more memories storing executable instructions that in response to execution by the one or more processors cause the apparatus to at least:

receive an indication of a purchase transaction of a client at a point of sale of a healthcare provider, the purchase transaction being applicable to a program of an administrator to which the client is enrolled, the program including one or more services; and in response to receipt of the indication of the purchase transaction;

send an electronic claim transaction submission for receipt by a primary payer separate and distinct from the administrator to initiate adjudication of a primary claim by the primary payer for an offset of at least a portion of a cost associated with the purchase transaction; and send the electronic claim transaction submission for receipt by the administrator to initiate adjudication by the administrator of one or more services of the program to which the purchase transaction is applicable, adjudication of the one or more services being separate and distinct from adjudication of the primary claim, the one or more services including one or more marketing services or interventions, wherein receipt of the electronic claim transaction submission by the administrator enables the administrator to provide the one or more services to the client in response to adjudication of the one or more services by the administrator.

8. The apparatus of claim 7, wherein the apparatus being caused to send the electronic claim transaction submission for receipt by the primary payer and for receipt by the administrator includes being caused to send the claim transaction submission formatted in accordance with the National Council for Prescription Drug Programs (NCPDP) Telecommunication Standard.

9. The apparatus of claim 7, wherein the apparatus being caused to send the electronic claim transaction submission for receipt by the administrator includes being caused to send the electronic claim transaction submission to enable the administrator to further determine a secondary benefit.

10. The apparatus of claim 9, wherein the apparatus being caused to send the electronic claim transaction submission for receipt by the primary payer includes being caused to send the electronic claim transaction submission to enable the primary payer to determine a primary benefit offsetting at least a portion of the cost associated with the purchase transaction, and wherein the apparatus being caused to send the electronic claim transaction submission for receipt by the administrator includes being caused to send the electronic claim transaction submission to enable the administrator to determine a monetary secondary benefit further offsetting the cost.

11. The apparatus of claim 7, wherein the purchase transaction comprises a purchase transaction for a good or service, wherein the apparatus being caused to send the electronic claim transaction submission for receipt by the administrator includes being caused to send the electronic claim transaction submission including information associated with the good or service, and wherein the apparatus being caused to send the electronic claim transaction submission for receipt by the administrator includes being caused to send the electronic claim transaction submission to enable the administrator to maintain, based on the received information, information regarding one or more of historical purchases of the good or service, a timing or a frequency of the historical purchases.

12. A non-transitory computer-readable storage medium having computer-readable program code portions stored therein that, in response to execution by one or more processors, cause an apparatus to at least:

receive an electronic claim transaction submission at an administrator in response to a purchase transaction of a client at a point of sale of a healthcare provider, a primary payer separate and distinct from the administrator also receiving the electronic claim transaction submission from the healthcare provider to initiate adjudication of a primary claim for an offset of at least a portion of a cost associated with the purchase transaction; and adjudicate, in response to receiving the electronic claim transaction submission at the administrator and separate and distinct from adjudication of the primary claim by the primary payer, one or more services of a program of the administrator to which the client is enrolled, the purchase transaction being applicable to the program, the one or more services including one or more marketing services or interventions;

wherein the apparatus is also caused to trigger provision of the one or more services to the client in response to adjudication of the one or more services.

13. The computer-readable storage medium of claim 12, wherein the apparatus is caused to receive the claim transaction submission formatted in accordance with the National Council for Prescription Drug Programs (NCPDP) Telecommunication Standard.

14. The computer-readable storage medium of claim 12, wherein the computer-readable storage medium has further computer-readable program code portions stored therein that, in response to execution by the one or more processors, cause the apparatus to further extract one or more items associated with the claim transaction submission in order to trigger provision of one or more additional services to the client.

15. The computer-readable storage medium of claim 12, wherein the apparatus being caused to adjudicate the one or more services includes being caused to further adjudicate one or more secondary benefits, the purchase transaction being applicable to the program and the one or more secondary benefits, and wherein the apparatus being caused to trigger provision of the one or more services includes being caused to further trigger provision of the one or more secondary benefits to the client in response to adjudication of the one or more secondary benefits.

16. The computer-readable storage medium of claim 15, wherein the primary payer has received the electronic claim transaction submission to enable the primary payer to determine a primary benefit offsetting at least a portion of the cost associated with the purchase transaction, and wherein the apparatus being caused to adjudicate the one or more secondary benefits includes being caused to determine a monetary secondary benefit further offsetting the cost, the secondary benefit being provided through the administrator.

17. The computer-readable storage medium of claim 12, wherein the purchase transaction comprises a purchase transaction for a good or service, and wherein the apparatus being caused to adjudicate the one or more services includes being caused to receive information associated with the purchase transaction for the good or service, and maintain, based on the received information, information regarding one or more of historical purchases of the good or service, a timing or a frequency of the historical purchases.

18. A non-transitory computer-readable storage medium having computer-readable program code portions stored therein that, in response to execution by one or more processors, cause an apparatus to at least:

receive an indication of a purchase transaction of a client at a point of sale of a healthcare provider, the purchase transaction being applicable to a program of an administrator to which the client is enrolled, the program including one or more services; and in response to receipt of the indication of the purchase transaction;

send an electronic claim transaction submission for receipt by a primary payer separate and distinct from the administrator to initiate adjudication of a primary claim by the primary payer for an offset of at least a portion of a cost associated with the purchase transaction; and send the electronic claim transaction submission for receipt by the administrator to initiate adjudication by the administrator of one or more services of the program to which the purchase transaction is applicable, adjudication of the one or more services being separate and distinct from adjudication of the primary claim, the one or more services including one or more marketing services or interventions, wherein receipt of the electronic claim transaction submission by the administrator enables the administrator to provide the one or more services to the client in response to adjudication of the one or more services by the administrator.

19. The computer-readable storage medium of claim 18, wherein the apparatus being caused to send the electronic claim transaction submission for receipt by the primary payer and for receipt by the administrator includes being caused to send the claim transaction submission formatted in accordance with the National Council for Prescription Drug Programs (NCPDP) Telecommunication Standard.

20. The computer-readable storage medium of claim 18, wherein the apparatus being caused to send the electronic claim transaction submission for receipt by the administrator includes being caused to send the electronic claim transaction submission to enable the administrator to further determine a secondary benefit.

21. The computer-readable storage medium of claim 20, wherein the apparatus being caused to send the electronic claim transaction submission for receipt by the primary payer includes being caused to send the electronic claim transaction submission to enable the primary payer to determine a primary benefit offsetting at least a portion of the cost associated with the purchase transaction, and wherein the apparatus being caused to send the electronic claim transaction submission for receipt by the administrator includes being caused to send the electronic claim transaction submission to enable the administrator to determine a monetary secondary benefit further offsetting the cost.

22. The computer-readable storage medium of claim 18, wherein the purchase transaction comprises a purchase transaction for a good or service, wherein the apparatus being caused to send the electronic claim transaction submission for receipt by the administrator includes being caused to send the electronic claim transaction submission including information associated with the good or service, and wherein the apparatus being caused to send the electronic claim transaction submission for receipt by the administrator includes being caused to send the electronic claim transaction submission to enable the administrator to maintain, based on the received information, information regarding one or more of historical purchases of the good or service, a timing or a frequency of the historical purchases.

* * * * *